US006408459B1

United States Patent
Lee

(12) United States Patent
(10) Patent No.: US 6,408,459 B1
(45) Date of Patent: Jun. 25, 2002

(54) TOILET BOWL EQUIPPED WITH FAR INFRARED LAMPS

(76) Inventor: Kum-Hoon Lee, 651-403 Shinnamushil Miju APT, 965-2 Youngtong-dong, Paldal-gu, Suwon-si, Kyoungki-do, 442-730 (KR)

( * ) Notice: Subject to any disclaimer, the term of this patent is extended or adjusted under 35 U.S.C. 154(b) by 0 days.

(21) Appl. No.: 09/744,319

(22) PCT Filed: May 24, 2000

(86) PCT No.: PCT/KR00/00521

§ 371 (c)(1),
(2), (4) Date: Jan. 19, 2001

(87) PCT Pub. No.: WO01/75239

PCT Pub. Date: Oct. 11, 2001

(30) Foreign Application Priority Data

Apr. 1, 2000 (KR) .......................................... 2000-9359

(51) Int. Cl.⁷ ................................................ A47K 13/00
(52) U.S. Cl. .................................. 4/661; 4/420; 4/233
(58) Field of Search .......................... 4/661, 309, 420, 4/222, 233

(56) References Cited

U.S. PATENT DOCUMENTS 2,440,231 A * 4/1948 Davidson ....................... 4/233
2,458,019 A * 1/1949 Niles ............................. 4/233
4,242,764 A * 1/1981 Fukuda ......................... 4/233
5,039,865 A * 8/1991 Koji ........................ 250/455.1
5,513,396 A * 5/1996 Tsipov .......................... 4/661
5,915,845 A * 6/1999 Lee .............................. 4/237
6,098,211 A * 8/2000 Ehrensperger et al. ......... 4/233

FOREIGN PATENT DOCUMENTS

JP 2243-121 B1 * 9/1990
JP 4-90732 B1 * 3/1992 ................... 4/309

* cited by examiner

Primary Examiner—Charles R. Eloshway
(74) Attorney, Agent, or Firm—Cantor Colburn LLP

(57) ABSTRACT

A toilet bowl equipped with far infrared lamps, by which users can bathe the genital organs and the anus region while sitting down on a toilet bowl seat for movement of bowel or urination at need without taking additional time. The toilet bowl comprises: front and rear holes formed on a toilet bowl body; first and second far infrared lamps respectively inserted into the front and rear holes for emitting far infrared rays, wherein the front and rear holes are formed in appropriate positions for making the far infrared lamps emit the far infrared rays to the genital organs and the anus region of women and men; first and second transparent heatproof lenses, each of which is disposed between the hole and the far infrared lamp; a first sensing means to be mounted on a ceiling, the first sensing means making the far infrared lamps turn on or off when a user sits on the toilet bowl seat; and ON and OFF switches for operating the far infrared lamps manually.

3 Claims, 4 Drawing Sheets

TOILET BOWL EQUIPPED WITH FAR INFRARED LAMPS

BACKGROUND OF THE INVENTION

This invention relates to a toilet bowl equipped with far infrared lamps, and more particularly, to a toilet bowl equipped with far infrared lamps, by which users can receive a treatment by far infrared rays while emptying the bowel without taking additional time.

There are well known applications related to toilet bowls and treatment devices equipped with far infrared lamps, for example, a bidet, a low-noise toilet bowl, a therapeutic far infrared device and a toilet bowl equipped with far infrared lamps which is attached on a front portion of a toilet bowl seat.

Furthermore, a toilet bowl seat with a number of protrusions for an acupressure effect and a moxacautery device is disclosed in a Korean Utility Model No. 20-174901. The toilet bowl seat includes a number of acupressure protrusions, a moxacautery nozzle and a far infrared sterilizer at the upper surface of the toilet bowl seat, thereby providing users with the acupressure effect, the moxacautery effect and the sterilizing effect by the far infrared ray while the users sit down on the toilet bowl seat.

Additionally, a toilet bowl seat equipped with an ultraviolet device and a far infrared device is disclosed in a Korean Utility Model Application No. 92-24951. At the front and lower surface of the toilet bowl seat, an ultraviolet lamp and a far infrared lamp, which are connected to a timer in a semicircle made of a crystal, are screwed into a socket and attached at a mounting plate. An ultraviolet lamp switch is mounted on the rear of a rotary shaft in such a manner that the ultraviolet lamp switch is connected to a power source when the toilet bowl cover is shut. A far infrared lamp switch is connected to the power source only when an adhesion pressure is applied to the toilet bowl seat.

However, the conventional products have several problems that a user must bathe in the far infrared ray with additional time, or the toilet bowl must have an additional cover equipped on the toilet bowl. The conventional products have another problems that they cannot emit the far infrared ray and/or the ultraviolet ray to an appropriate position, i.e., surroundings of the genital organs and the anus region because the lamp, which is mounted at the front portion of the toilet bowl seat, is located above the location of the user's genital organs and the anus region. Furthermore, the conventional products have further problems that they have a restricted intensity of far infrared ray heat, for example, the user may get burnt, and a sensitive bulb may be damaged when the toilet seat is raised or lowered.

SUMMARY OF THE INVENTION

It is, therefore, an object of the present invention to provide a toilet bowl equipped with far infrared lamps, in which a first far infrared lamp located at a front and lower surface of the toilet bowl radiates electromagnetic waves to a woman's vulva and a man's penis while users are sitting down on the toilet bowl seat for bowel movement or urination without additionally equipping a seat cover separated from the toilet bowl or without taking additional time for the radiation, so that the users can always maintain a clean condition.

It is another object of the present invention to provide a toilet bowl equipped with far infrared lamps, in which a second far infrared lamp located at a rear and lower surface of the toilet bowl radiates electromagnetic waves to the user's anus region exactly, thereby improving the circulation of the blood and treating and preventing hemorrhoids.

To accomplish the above objects, the present invention provides a toilet bowl equipped with far infrared lamps, comprising: front and rear holes, which are formed at appropriate parts of a toilet bowl body corresponding to users' genital organs and the anus region; a first and a second far infrared lamps respectively inserted into the front and rear holes for emitting far infrared rays, wherein the front and rear holes are formed in an exact positions for making the far infrared lamps emit the far infrared rays to the genital organs and the anus region of women and men; a first and a second transparent heatproof lenses, each of which is disposed between the hole and the far infrared lamp, each of the transparent heatproof lens serving for heatproof, insulation and waterproof; a sensing means mounted on a ceiling and a sensing switch for activating arid deactivating the sensing means, the sensing means, when activated, detecting a user and providing automatic operation of the far infrared lamps; and ON and OFF switches for operating the far infrared lamps manually.

By mounting the first and second far infrared lamps into the front and rear holes formed on the toilet bowl body and mounting the transparent heatproof lenses for waterproof, the users can conveniently use the toilet bowl with the treatment effect by far infrared rays.

BRIEF DESCRIPTION OF THE DRAWINGS

Further objects and advantages of the invention can be more fully understood from the following detailed description taken in conjunction with the accompanying drawings in which.

DETAILED DESCRIPTION OF THE PREFERRED EMBODIMENT

Figure 1:
FIG. 1 is a perspective view of a conventional toilet bowl.

Referring now to the drawings, like reference numerals designate corresponding parts throughout several views.

Figure 2:
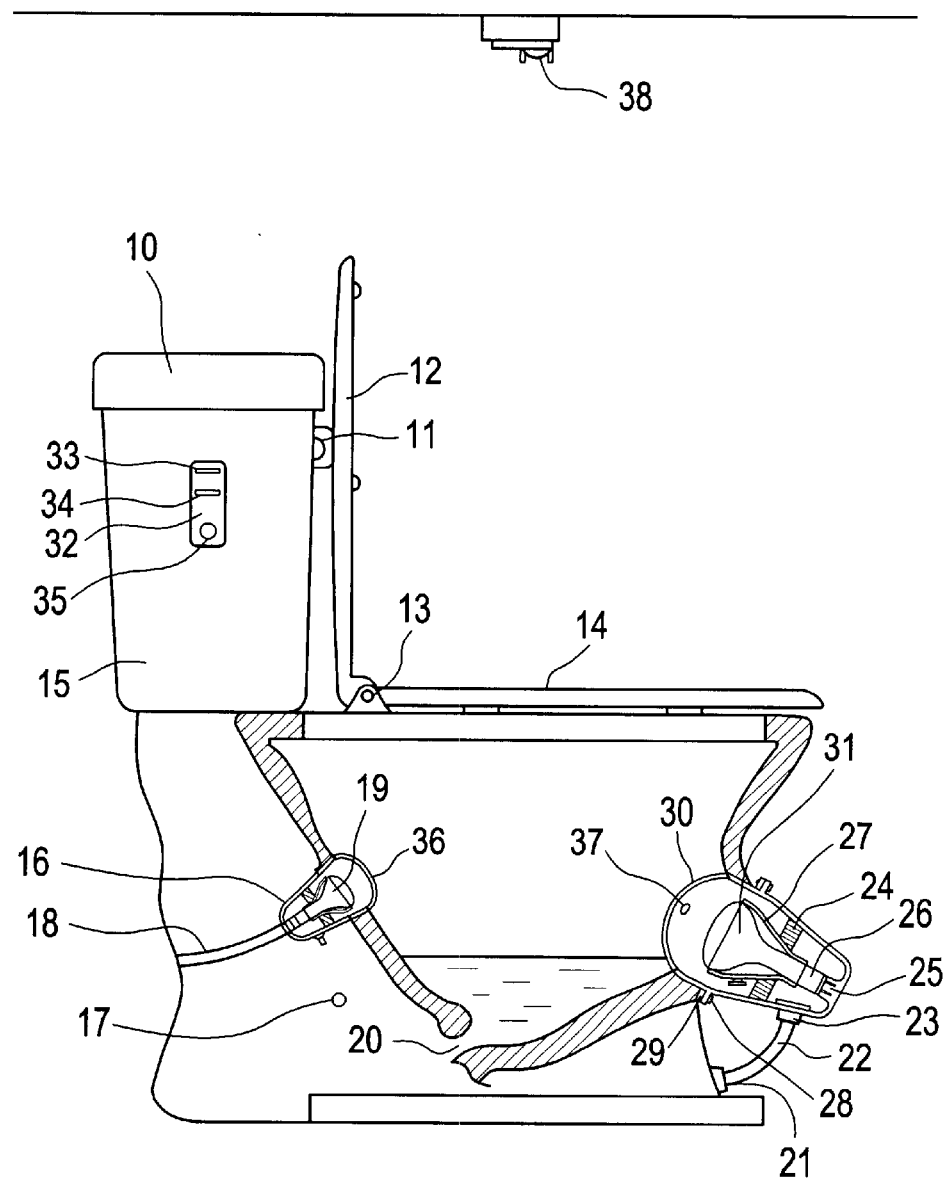
FIG. 2 is a detailed view of a toilet bowl equipped with far infrared lamps according to the present invention.
Figure 3:
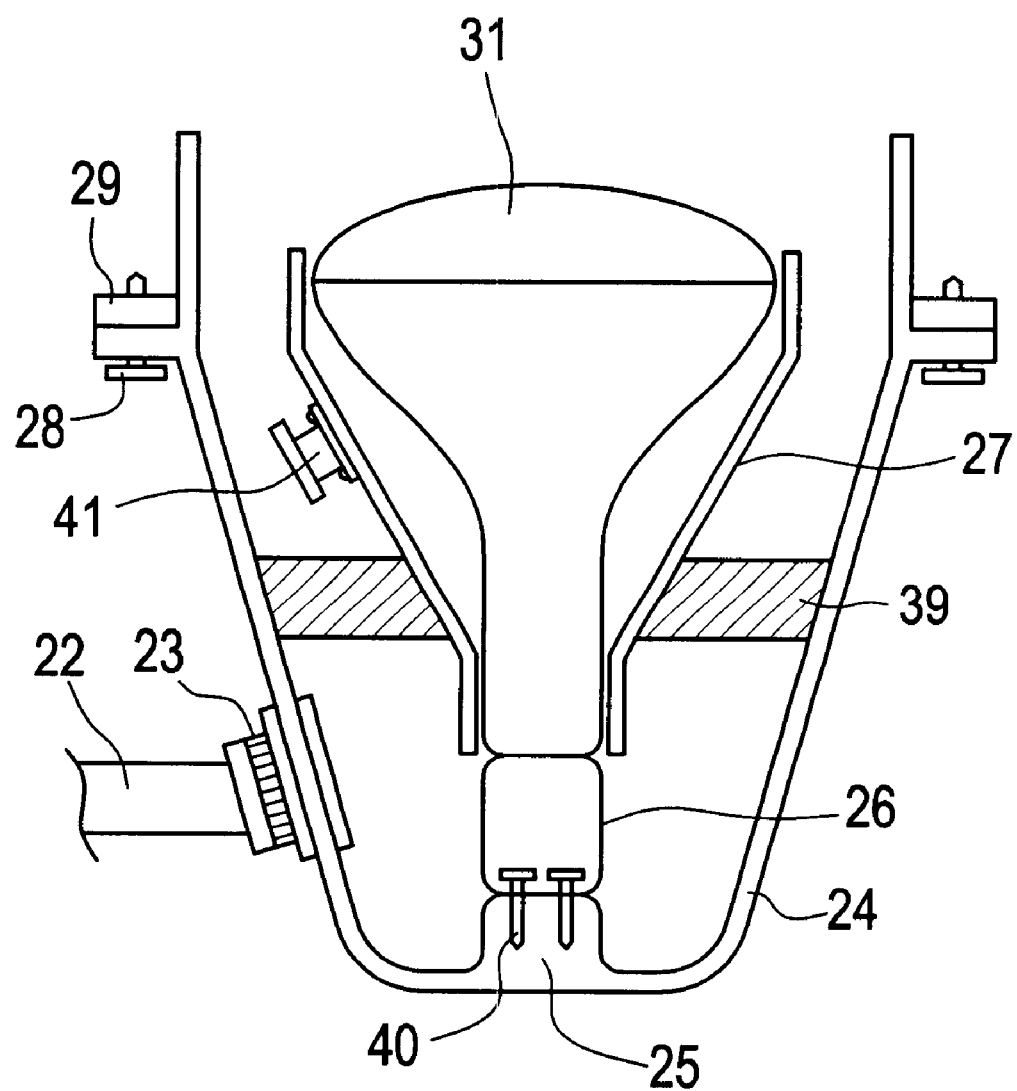
FIG. 3 is an expanded sectional view of the far infrared lamp according to the present invention.
Figure 4:
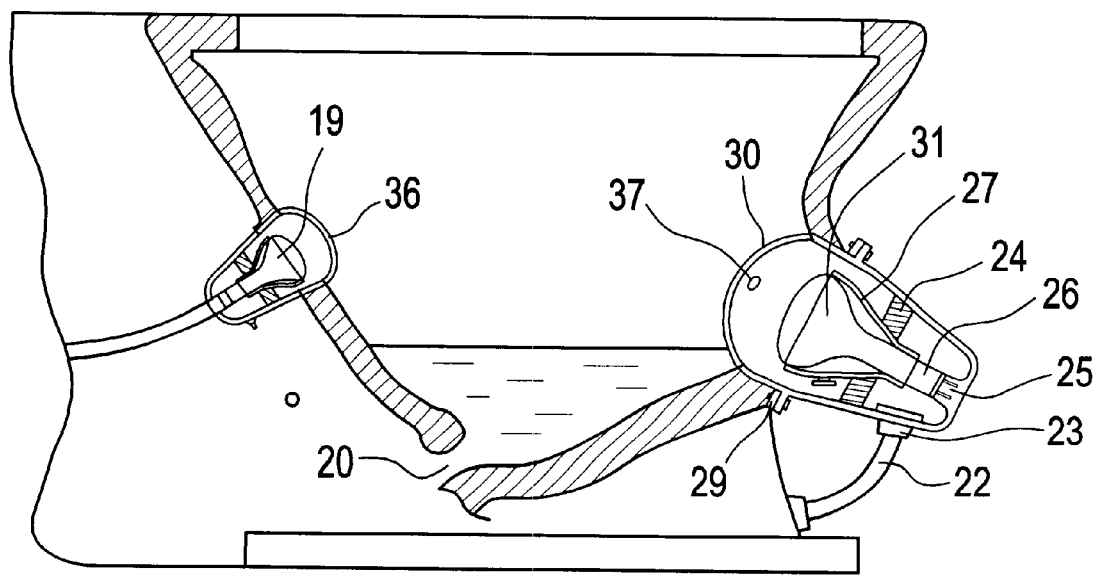
FIG. 4 is a sectional view of a side lower portion of the toilet bowl with far infrared lamps according to the present invention.

FIG. 1 is a perspective view of a conventional toilet bowl and FIG. 2 is a detailed view of a toilet bowl equipped with far infrared lamps according to the present invention. FIG. 3 is an expanded sectional view of the far infrared lamp according to the present invention and FIG. 4 is a sectional view of a side lower portion of the toilet bowl equipped with far infrared lamps according to the present invention. Referring to the drawings, there are a water tank lid 10, a water draining switch 11, a toilet bowl seat cover 12, a seat fixing portion 13, a toilet bowl seat 14, a water tank 15, a rear hole 16, a toilet bowl body 17, a second far infrared lamp passage 18, a second far infrared lamp 19, an excrement outlet 20, an outlet 21 of air circulation and electric current output line, a passage 22 of air circulation and electric current flow, an inlet 23 of air circulation arid electric current input line, a first far infrared lamp box 24, an insulated cap fixing portion 25, an insulating socket 26, a heatproof cap 27, a fixing bolt 28, a silicone rubber packing 29, a first transparent heatproof lens 30, a first far infrared lamp 31, a switch body 32, an ON/OFF switch 33 and 34, a sensor switch 35, a second transparent heatproof lens 36, a front hole 37, a sensing means 38 mounted on a ceiling, a heatproof cap fixing portion 39, a socket fixing bolt 40 and a heat sensor 41.

Referring to FIG. 2, the toilet bowl has the rear hole 16 formed at somewhat lower portion from the center of the toilet bowl body 17 and the front hole 37 formed at somewhat lower portion from the center of the toilet bowl body 17. The first far infrared lamp 31 and the second far infrared lamp 19 are respectively mounted in the holes 37 and 16 so as for users not to feel inconvenience in use at all. The transparent heatproof lenses 30 and 36, which cover the first and second far infrared lamps 31 and 19, provide waterproofing effect during draining water.

As shown in FIG. 2, the rear and front holes 16 and 37 are formed at appropriate positions in such a manner that the far infrared lamps, which are inserted into the holes 16 and 37, radiate exactly the electromagnetic waves to the genital organs and the anus region. The transparent heatproof lenses 30 and 36 designed to pass the light are disposed at the holes for heatproof and insulation. Because the first far infrared lamp 31 is perfectly fixed at somewhat lower portion from the front and center portion of the toilet bowl body 17 without movement, there is no damage and trouble of the lamp or bulb. The second far infrared lamp 19 is also perfectly fixed at somewhat lower portion from the rear and center portion of the toilet bowl body 17.

As shown in FIG. 2, the far infrared lamps 19 and 31 are designed in such a manner that the far infrared lamps 19 and 31 can be detachably mounted at the outside of the toilet bowl.

The first far infrared lamp box 24 of the toilet bowl body 17 is designed in such a manner that the first far infrared lamp 31 is connected with the insulating socket 26, the far infrared lamp box 24 is fixed to the far infrared lamp 31 through a screw so that the electric current flows through the passage line 22. Waterproofing caps 21 and 23 are attached to the outlet 21 and the inlet 23 of the passage 22 to have the waterproofing effect. The heat-proofing cap 27 made of a heat-proofing material is attached to the far infrared lamp 31, so that the heat produced when the first far infrared lamp 31 is worked can be blocked.

The first far infrared lamp box 24 of the toilet bowl body 17 is designed in such a manner that the first far infrared lamp 31 is connected with the insulating socket 26, the far infrared lamp box 24 is fixed to the far infrared lamp 31 through a screw so that the electric current flows through the passage line 22. Waterproofing caps are attached to the outlet 21 and the inlet 23 of the passage 22 to have the waterproofing effect. The heat-proofing cap 27 made of a heat-proofing material is attached to the far infrared lamp 31, so that the heat produced when the first far infrared lamp 31 is worked can be blocked.

The far infrared lamp device is automatically turned on or off by the sensing means 38 which is mounted on the ceiling. The sensor switch 35 allows for activation and deactivation of the sensing means 38. When activated, the sensing means 38 detects the presence or absence of a user, and automatically turns on or off the far infrared lamp device accordingly. Furthermore, the far infrared lamp device can be operated manually and conveniently if the users press the ON/OFF switch 33 and 34 disposed in an appropriate position on one side of the water tank 15.

As described above, the present invention facilitates the blood circulation of the surroundings of the genital organs, has a disinfection effect of the inside of the toilet bowl, makes the anus region clean, and treats and prevents anus diseases and genital organs diseases.

Moreover, the present invention facilitates the treatment and the prevention of genital organs diseases and anus diseases without additionally using a thermotherapeutic sitz bath and without taking additional time.

Therefore, the present invention is needed for persons, who have difficulties in using medical devices periodically and frequently, and it saves time because the far infrared rays radiating from the far infrared lamp are emitted to the users' genital organs and the anus region while the users sit down on the toilet bowl seat for bowel movement or urination.

Having now described above embodiment, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention.

What is claimed is:

1. A toilet bowl equipped with far infrared lamps, comprising:

front and rear holes, which are formed at a lower portion of a toilet bowl body;

first and second far infrared lamps respectively inserted into the front and rear holes for emitting far infrared rays, wherein the front and rear holes are formed in appropriate positions for making the far infrared lamps emit the far infrared rays to the genital organs and the anus region of women and men when a user sits down on a toilet bowl seat;

first and second transparent heatproof lenses, each of which is disposed between the hole and the far infrared lamp;

a sensing means to be mounted on a ceiling for detecting the user and providing automatic operation of the far infrared lamps;

a sensor switch for activating the sensing means; and an ON and OFF switch for manually operating the far infrared lamps.

2. A toilet bowl equipped with far infrared lamps as claimed in claim 1, wherein the toilet bowl body includes at least two or more far infrared lamps.

3. A toilet bowl equipped with far infrared lamps as claimed in claim 1, wherein the toilet bowl further comprises an outlet for air circulation and electric current output line, a passage for air circulation and electric current flow, and an inlet for air circulation and electric current input line.

* * * * *